United States Patent [19]

Ward et al.

[11] 4,414,084

[45] Nov. 8, 1983

[54] PROCESS FOR CONVERSION OF CELLULOSE TO AMINO ACIDS BY RADIOFREQUENCY PLASMA OF NITROGEN AND HYDROGEN

[75] Inventors: Truman L. Ward; Ruth R. Benerito, both of New Orleans, La.

[73] Assignee: The United States of America as represented by the Secretary of Agriculture, Washington, D.C.

[21] Appl. No.: 409,268

[22] Filed: Aug. 18, 1982

[51] Int. Cl.$^3$ ............................................. C07G 13/00
[52] U.S. Cl. .................................................. 204/165
[58] Field of Search ........................ 204/164, 165, 177

[56] References Cited

PUBLICATIONS

Ward et al., "Synthesis of Nitrogenous Polymers by RF Cold Plasma Techniques", Organic Coatings and Plastic Chemistry, vol. 45, pp. 382–387, American Chemical Society (1981).

T. L. Ward, H. Z. Jung, O. Hinojosa, R. R. Benerito, J. Surface Sci. 76,257 (1978).

T. L. Ward, H. Z. Jung, O. Hinojosa and R. R. Benerito, J. Appl. Poly. Sci. 23, 1987 (1979). L.S. Miller and H. C. Urey, Science 130, 245 (1959).

J. R. Holland and C. F. Emanuel, Biochem Biophys. Acta 208, 317 (1970).

*Primary Examiner*—John F. Niebling
*Attorney, Agent, or Firm*—M. Howard Silverstein; David G. McConnell; Raymond C. Von Bodungen

[57] ABSTRACT

This invention relates to a process for converting cellulose to amino acids by radiofrequency plasma of nitrogen and hydrogen gases. Cellulose is placed between the electrodes in a radiofrequency plasma reaction chamber which is sealed and maintained at a reduced pressure. Hydrogen and nitrogen mixture is bled through the chamber and sufficient radiofrequency electric current applied until the cellulose is consumed, thereby producing a mixture of amino acids. The cellulose can be either cotton or wood derivatives.

7 Claims, No Drawings

PROCESS FOR CONVERSION OF CELLULOSE TO AMINO ACIDS BY RADIOFREQUENCY PLASMA OF NITROGEN AND HYDROGEN

BACKGROUND OF THE INVENTION (1) Field of the Invention

This invention relates to a process for converting cellulose to amino acids. More particularly, this invention relates to a process for converting cellulose to amino acids by exposing it to a radiofrequency plasma of a mixture of nitrogen and hydrogen.

(2) Description of the Prior Art

Heretofore, plasmas of gaseous hydrocarbons such as carbon monoxide or methane and ammonia or a mixture of nitrogen and hydrogen have resulted in formation of amino acids. It has also been reported that radiofrequency (rf) plasma of argon, nitrogen or air can be used to make cotton absorb either oil or water more rapidly. T. L. Ward, H. Z. Jung, O. Hinojosa and R. R. Benerito, J. Surface Sci. 76, 257 (1978). Free radical sites created by the plasma picked up oxygen from moisture or air and chemiluminesced The free radicals could initiate polymerization post plasma. T. L. Ward, H. Z. Jung, O. Hinojosa and R. R. Benerito, J. Appl. Poly. Sci. 23, 1987 (1979). Irradiation of cotton with any of the aforementioned plasmas resulted in addition of nitrogen to the cotton, which was readily detected by electron spectroscopy for chemical analysis (ESCA), but was not detected by multiple internal reflectance spectroscopy (MIR). Except for hydrogen produced by plasma effects on cotton or derived from water absorbed on the reactor walls, there was none in the plasma system.

Miller and Urey (S. L. Miller and H. C. Urey, Science 130, 245 (1959)) reported formation of amino acids and other organic materials by electric discharge in mixture of methane, ammonia, hydrogen and water, and Hollahan and Emanuel (J. R. Holland and C. F. Emanuel, Biochim. Biophys. Acta 208, 317 (1970)) produced protein-like materials by subjecting a mixture of CO, $N_2$, and $H_2$ to an rf field (13.56 MHz). In both of these instances hydrogen cyanide and formaldehyde were shown to be precursors of the amino acids.

SUMMARY OF THE INVENTION

This invention relates to a process for producing amino acids from cellulose. Cellulose is positioned between or near the electrodes in a radiofrequency plasma reaction chamber. The chamber is sealed and the pressure inside reduced. A mixture of hydrogen and nitrogen gases is continuously bled through the chamber while the reduced pressure is maintained. Radiofrequency electric current is applied to the electrodes with sufficient power to create a colored plasma in the reaction chamber for a sufficient period of time to consume the cellulose or until for any other reason the reaction ceases. The result is a mixture of amino acids from the cellulose.

This process is a considerable improvement over the prior art because heretofore it was necessary to use plasmas of gaseous hydrocarbons such as carbon monoxide or methane and either ammonia or a mixture of nitrogen and hydrogen to get a resultant amino acid formation. Contrastingly, the preferred embodiment of this invention uses a cellulose in the solid state and thus the carbon and oxygen for the amino acid structure is derived from solid cellulose.

DESCRIPTION OF THE PREFERRED EMBODIMENTS

This invention deals with the irradiation of cotton in rf plasmas containing nitrogen and hydrogen either as mixtures of $N_2$ and $H_2$ or as $NH_3$ gas. in contrast to the prior art, the cellulose is in the solid state and the carbon and oxygen for the amino acid structure is derived from solid cellulose.

In general, in accordance with the preferred embodiment, the cellulose material is placed in the radiofrequency plasma reactor in a location between, or adjacent to, the electrodes. An essential part of the process of this invention is the location of the cellulose so that the molecular structure of the cellulose is disrupted in plasma near the electrodes and molecular substructure from cellulose is carried downstream as the plasma flows away from the electrodes where union with nitrogen and hydrogen forms the amino acid material which is deposited on a glass or other nonconducting collector surface. In carrying out the process of the invention, the cellulose may be irradiated in the plasma until it is consumed.

Substantially, any cellulosic material can suitably be employed in the present process.

In generating the plasma, substantially any radiofrequency electric field can be employed although frequencies in the 10 to 100 megahertz range are preferred.

Although substantially any mixture of nitrogen and hydrogen can be expected to yield some amino acid material, in the preferred embodiment, hydrogen to nitrogen ratios of from about 1:1 to about 3:1 give better yields of the desired product.

In carrying out the preferred process, a layer of cellulosic material is located between the electrodes. A flat glass collector plate is placed in the reaftor between the outlet to the vacuum pump and the electrodes. The reactor is closed and evacuated to a pressure of about 10 to 1000 millitorrs pressure. A mixture of hydrogen and nitrogen gases in the ratio of from about 1:1 to 3:1 is allowed to bleed into the reactor between the electrodes as reduced pressure is maintained. A radiofrequency field is applied to the electrodes and the power level adjusted to create a colored plasma flow through the reactor from the gas inlet toward the vacuum pump. This plasma is maintained until the cellulose has been consumed. When the cellulose is all consumed, the radiofrequency field is turned off, the vacuum pump is turned off and the reactor pressure is restored to atmospheric for removal of the collector plate. By virtue of the process of this invention, amino acid material is deposited in the plasma flow downstream from the electrodes toward the outlet to the vacuum pump and is collected on the glass plate.

The following examples illustrate, but do not limit the scope of the invention:

EXAMPLE 1

A layer of purified cotton cellulose measuring 1.5×4 cm and weight 0.8675 g. was placed horizontally in the radiofrequency plasma reaction chamber between the electrodes located one above and one below the sample and external to the glass reactor vessel. A glass collector plate was located inside the reactio just upstream from the outlet to the vacuum pump. Both cellulose and collector plate were in the colored plasma flow. The reactor was sealed and pumped to a reduced pressure measuring 25 millitorrs. A mixture of 1 part of molecular hydrogen with 1 part of molecular nitrogen was bled into the reactor through an inlet located between the electrodes. The reactor pressure was stabilized at 150 militorrs. The radiofrequency generator tuned to 13.56 megahertz was turned on and the output power adjusted to 40 watts. These conditions were maintained for the duration of the experiment. Irradiation was continued until the cellulose was consumed or for about six hours. The radiofrequency generator was turned off, the pressure restored to atmospheric, the collector plate removed and the collected material analyzed. UV showed no aromatic groups or conjugation. A ninhydrin test showed that the material had primary or secondary amine groups. The material was examined for amino acid content which was as follows:

| AMINO ACID | µg/ml |
| --- | --- |
| Alanine | 22.2 |
| Valine | 3.4 |
| Glycine | 122.1 |
| Isoleucine | 4.5 |
| Leucine | 6.0 |
| Proline | 3.8 |
| Threonine | 4.0 |
| Serine | 20.3 |
| Methionine | 4.4 |
| Hydroxyproline | 2.4 |
| Phenylalanine | 15.5 |
| Aspartic Acid | 30.0 |
| Glutamic Acid | 26.1 |
| Tyrosine | 3.1 |
| Lysine | 6.1 |
| Histidine | 7.1 |
| Arginine | 3.9 |
| Crystine/2 | |
| Tryptophan | |
| Total µg/ml | 284.9 | and concentration of sample sent was 300 µug/ml solid material vs almost 100% amino acid material.

EXAMPLE 2

The process of Example 1 except that purified wood pulp paper was used in place of purified cotton cellulose. The resultant product was the same as for Example 1.

EXAMPLE 3

The process of Example 1 except that the radiofrequency power level was doubled. The resultant product was the same product, but was deposited more rapidly.

EXAMPLE 4

The process of Example 1 except that the purified cotton cellulose was placed away from the electrodes. The cellulose was not consumed by the plasma and no amino acid material was deposited on the collector plate illustrating the necessity of locating the cellulose as close to the electrodes as feasible.

EXAMPLE 5

The process of Example 1 except that the ratio of molecular hydrogen to molecular nitrogen was 3:1 rather than 1:1. The same product was formed as in Example 1.

We claim:
1. A process for producing a mixture of amino acids from cellulose which process comprises:
    (a) positioning cellulose between or near electrodes in a radiofrequency plasma reaction chamber;
    (b) sealing and then reducing the pressure in said chamber;
    (c) bleeding a mixture containing a sufficient ratio of hydrogen and nitrogen through the chamber while maintaining the reduced pressure so that the hydrogen and nitrogen can react with the cellulose to form amino acids;
    (d) applying a radiofrequency electric current to the electrodes with sufficient power to create a colored plasma in the reaction chamber for a sufficient period of time to consume the cellulose thereby producing a mixture of amino acids from the cellulose.

2. The process of claim 1 including an additional step of shutting off: The electric supply, the vacuum, the flow of hydrogen and nitrogen gases and restoring the chamber to atmospheric pressure.

3. The process of claim 1 where the ratio of hydrogen to nitrogen is between 1:1 and 3:1.

4. The process of claim 1 wherein the cellulose is cotton.

5. The process of claim 1 wherein the cellulose is derived from wood.

6. The process of claim 1 wherein the radiofrequency is between about 10 and 100 megahertz.

7. The process of claim 1 wherein the pressure inside the reaction chamber was reduced and maintained between about 10 and 1000 millitorrs.

* * * * *